United States Patent [19]

Gilman

[11] Patent Number: 5,176,620

[45] Date of Patent: Jan. 5, 1993

[54] HEARING AID HAVING A LIQUID TRANSMISSION MEANS COMMUNICATIVE WITH THE COCHLEA AND METHOD OF USE THEREOF

[76] Inventor: Samuel Gilman, 11920 Dorothy St., Los Angeles, Calif. 90049

[21] Appl. No.: 599,066

[22] Filed: Oct. 17, 1990

[51] Int. Cl.⁵ ............................................. H04R 25/00
[52] U.S. Cl. ................................ 600/25; 128/420.006
[58] Field of Search ........................ 128/420.6; 600/25

[56] References Cited

U.S. PATENT DOCUMENTS

| | | | |
|---|---|---|---|
| 4,357,497 | 11/1982 | Hochmair et al. | 128/420.6 |
| 4,606,329 | 8/1986 | Hough | 128/421 |
| 4,988,333 | 1/1991 | Engebretson et al. | 128/420.6 |
| 5,085,628 | 2/1992 | Engebretson et al. | 600/25 |

Primary Examiner—William E. Kamm
Assistant Examiner—Scott M. Getzow
Attorney, Agent, or Firm—Timothy T. Tyson

[57] ABSTRACT

A hearing aid (100) is provided for surgically implanting in the ear of a subject. A liquid filled tube (142) is positioned between an orifice of the cochlea and a subcutaneous amplifier (200). A microphone (122) converts sound waves outside the subject into electrical signals which are amplified by the amplifier and are converted back into amplified mechanical motion by a transducer means (124). The amplified mechanical motion is transmitted through the tube by the liquid to the cochlea bypassing the outer and middle ears. The liquid and dimensions of the tube are selected to substantially match the acoustic impedance of the cochlea at the distal end of the tube.

51 Claims, 5 Drawing Sheets

HEARING AID HAVING A LIQUID TRANSMISSION MEANS COMMUNICATIVE WITH THE COCHLEA AND METHOD OF USE THEREOF

TECHNICAL FIELD

The present invention pertains to hearing aids, and more particularly to hearing aids utilizing a liquid transmission means.

BACKGROUND ART

The ear directs, amplifies, and converts sound waves into nerve impulses which are interpreted by the brain. The outer ear or pinna directs the sound waves into the auditory canal terminating at the eardrum or tympanic membrane. Attached to the tympanic membrane on the other side is the malleus, the first of three small bones in the middle ear called the ossicles. The other ossicles are the incus and the stapes. When the eardrum moves in response to the sound waves, the malleus articulates with the incus which in turn articulates with the stapes thereby transmitting the mechanical movement of the eardrum through the middle ear. In addition, the ossicles amplify the mechanical movement by their leveraged relationships. The foot plate of the stapes is attached to a covered resilient oval window in the fluid filled inner ear or cochlea. As the oval window moves in response to the mechanical movement of the stapes, pressure waves are transmitted into the liquid filled cochlea which transduces the pressure waves into electrical signals that in turn are sensed by nerves inside the cochlea. In addition to transmitting the mechanical movement, the oval window amplifies the pressure of the wave appearing at the eardrum because its area is smaller than that of the eardrum. In a normal ear, the mechanical advantage of the ossicles, together with the ratio of the oval window area to the eardrum area, provides a 20 times gain in sound pressure delivered to the cochlea.

Two broad categories of hearing loss are conduction loss and sensorineural (nerve) hearing loss. Conduction hearing loss refers to problems in the conduction of sound from the eardrum to the cochlea while sensorineural loss refers to losses due to defects in the cochlea, the cochlear nerves or the auditory centers of the brain. Measures to alleviate hearing deterioration vary depending on the part of the hearing system that is involved. Apparatus has been designed to amplify acoustical energy and apply it either through its normal path or by vibrating some part of the ossicles. Examples of the former have been available for years. Examples of the latter include implanted magnetic materials, coils, and piezo-electric materials in contact with the ossicles. A third type of apparatus stimulates the cochlear nerves electrically but has a significant disadvantage by requiring the user to relearn the significance of the signals received. A detailed survey of these types of devices is given in U.S. Pat. No. 4,850,962 to Schaefer.

For example, U.S. Pat. No. 3,882,285 to Nunley et al. shows an implant taking sound energy from the auditory canal and stimulating the ossicular chain via a direct mechanical link. U.S. Pat. No. 4,606,329 to Hough uses magnetic coupling through the skin to a coil implanted in the skull. This coil feeds signals in turn to a coil embedded near the middle ear cavity which induces mechanical motion in magnetic material attached to some part of the ossicular chain. In U.S. Pat. Nos. 4,850,962 and 4,729,366 to Schaefer, one of the ossicular bones is removed and mechanical vibration of the tympanic membrane is converted, in an implant, to an electrical signal by a transducer mounted proximate to the terminated ossicular chain. The electrical signals are then applied across the interrupted chain to the promontory of the cochlea or through a hole in the oval window or converted into mechanical motion which is transmitted to the stapes. Other devices are shown in U.S. Pat. Nos. 3,870,832 to Fredrickson; 4,052,754 to Homsy; 4,063,048 to Kissiah; 4,357,497 to Hochmair et al.; and 4,696,287 to Hortmann. Publications of background interest are Hough J. et al. "Experiences with implantable hearing devices and a presentation of a new device" *Anno Otol Rhinol Laryngol* 95: 1986 60–65, Suzuki J. et al. "Middle ear implant for humans." *Acta Otolaryngol* 1985:99 313–317, and Hough J. et al. "A middle ear implantable hearing device for controlled amplication of sound in the human: a preliminary report" *Laryngoscope* 97: February 1987, 141–151.

A fourth type of device produces amplified sound waves in the middle ear. In U.S. Pat. No. 3,346,704 to Mahoney, such a device is described in which a sound receiving and amplifying unit is implanted in the mastoid antrum with a "microphone tube" beginning at a point just under the skin inside the ear canal and a "speaker tube" extending from a speaker into the middle ear space. However, Mahoney has a significant disadvantage in that when acoustical energy from the air is applied directly to the oval window instead of being conducted from the eardrum through the ossicles, the sound transfer is very much reduced because of the greater acoustic impedance of the liquid-filled cochlea compared to that of air. The impedance matching effect provided by the mechanical advantage of the ossicles, together with the ratio of the oval window area to the eardrum area, is lost if the sound energy is introduced directly into the middle ear space.

DISCLOSURE OF INVENTION

The present invention is directed to a liquid transmission means for transmitting acoustical energy to the cochlea. In a preferred embodiment, the liquid transmission means is a liquid filled tube which is surgically inserted through the middle ear to an orifice in the cochlea. The liquid filled tube acts as a transmission line with little losses because the liquid can be similar in acoustic properties to the perilymph in the cochlea and the impedance of the transmission line can be more closely matched to the acoustic impedance of the cochlea at the termination of the tube at the cochlea.

In accordance with one important aspect of the invention, an electro-mechanical means is provided that converts acoustical energy processed through microphone, amplifier, and transducer means to mechanical motion for application to the liquid transmission means. In a preferred embodiment, the electro-mechanical means is housed in a biologically inert material such as titanium and is implanted with the microphone means subcutaneously behind the ear or near the auditory canal.

In accordance with another important aspect of the invention, a method is provide for improving the hearing of a hearing impaired subject comprising the steps of placing a liquid transmission means from a proximal end to a distal end in operative association with an orifice of the cochlea, filling the liquid transmission means with liquid, converting sound energy to mechanical motion, and applying the mechanical motion to the proximal end of the transmission means.

The novel features of the invention are set forth with particularity in the appended claims. The invention will be best understood from the following description when read in conjunction with the accompanying drawings.

MODES FOR CARRYING OUT THE INVENTION

Figure 1:
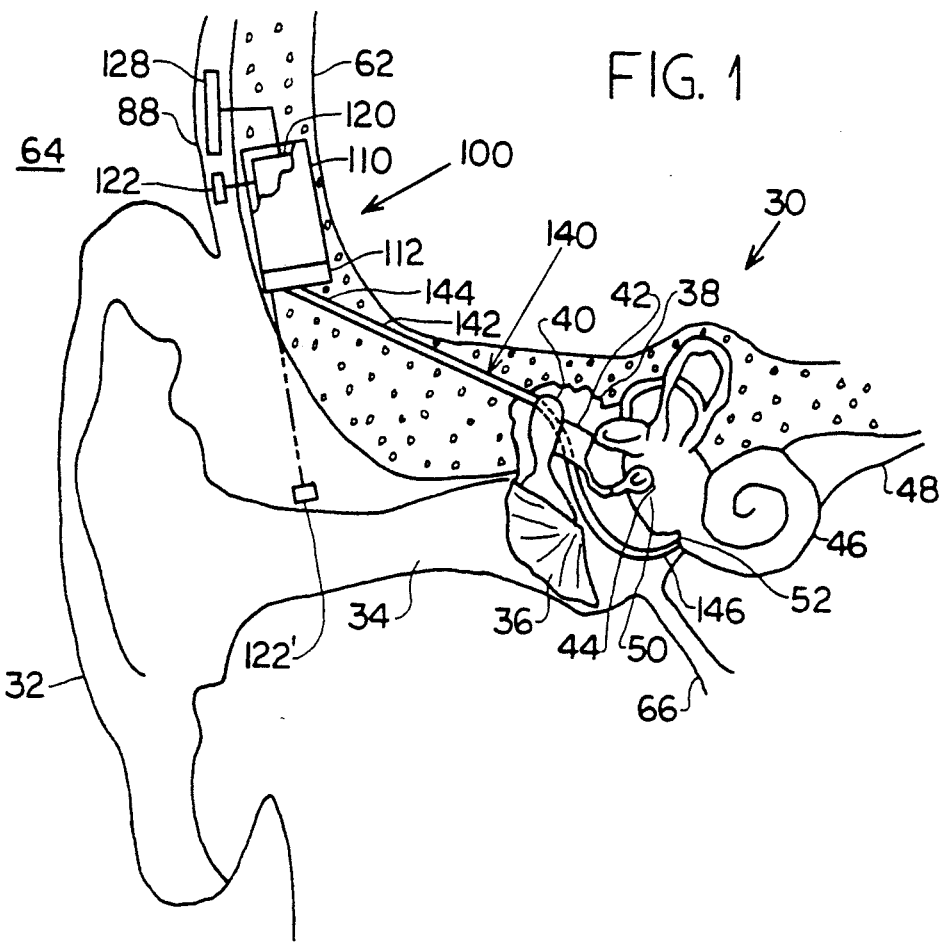
FIG. 1 is a sectional elevation view of the human hearing system illustrating an implanted hearing aid in accordance with an embodiment of the present invention.

An embodiment, in accordance with the present invention, of a hearing aid 100 is illustrated in FIG. 1 in operative association with the hearing systems 30. The enclosure 110 is implanted in the mastoid bone 62. A liquid transmission means 140 in the form of a liquid filled tube 142 is also implanted in the mastoid bone 62. The proximal end 144 of the liquid filled tube 142 connects through a coupler 112 to the enclosure 110 while the distal end 146 is inserted through the middle ear cavity 38 to the round window 52 of the cochlea 46. Electro-mechanical means 120 housed in the enclosure 110 converts acoustical energy received by microphone means 122 from the outer environment 64 via skin flap 88 into mechanical motion which is transmitted by the liquid filled tube 142. An alternate position 122' for the microphone adjacent the auditory canal 34 may also be used. An induction coil 128 is mounted under the skin flap 88 for receiving magnetic energy from an external source for recharging the battery (shown in FIG. 4) of the electro-mechanical means 120.

The hearing system 30 includes the outer ear 32; the auditory canal 34; the eardrum or tympanic membrane 36; the ossicular chain made up of malleus 40, the incus 42, and the stapes 44; the cochlea 46; and the cochlear nerve 48. Also illustrated is the eustacian tube 66 which equalizes pressures in the middle ear to that in the environment. In a normal ear, acoustical energy reaches the eardrum through the outer ear and the auditory canal where it causes the eardrum to vibrate. These vibrations are transmitted through the ossicular chain to the cochlea where they are converted into nerve impulses which are sent to the brain through the cochlear nerve. The present invention bypasses conduction hearing loss problems by going directly to the cochlea.

The features of this invention distinguish it from previous approaches to implantable hearing aids. Many of these features are involved in the acoustics of transmitting sound into the ear and in particular the use of tubes for transmitting such sound through different media contained in the tubes. A part of this invention is the selection of liquids which are compatible with the liquid (perilymph) in the scala vestibuli or scala tympani of the human cochlea (inner ear). Such selection can include liquids whose acoustic characteristics are such as to maximize the conduction of sound into the cochlea. An example of a liquid other than perilymph but which has almost identical acoustical properties is sea water, whose density, coefficient of viscosity and characteristic acoustic impedance are almost the same.

The advantages of the liquid filled tube of the present invention in comparison to the air filled tubes of the prior art can be made on the basis of viscous losses in the medium, losses due to impedance mismatches during transmission, and losses due to impedance mismatches during the transfer of sound into the cochlea. Losses due to viscous friction are about 29 times greater in a tube containing air at room temperature than in sea water in the same tube even though the kinematic coefficient of viscosity of sea water is considerably greater (about 6.5 times) than the corresponding viscosity of air (*Fundamentals of Acoustics*, by Kinsler & Frey, John Wiley & Sons, ©1962, pp. 240, 503). These losses are proportional to a function of both frequency and the bore of the tube and are negligible in a sea-water filled tube compared to a significant loss in air.

Impedance mismatch such as when going from one bore size to another or when going from one medium to another create losses due to reflections of sound from the impedance transition. For example, sound going from a 2 millimeter bore air filled tube into the air space of the middle ear can suffer a reduction in sound energy level of about 88% so that only about 12% of the incoming sound is available for use (*Fundamentals*, supra, pp. 131-133). Similarly, the transfer of the sound in the air of the middle ear to the cochlea via the oval (or round) window suffers a further decline. For the average ear, the reduction in sound is approximately 20:1 so that only 5% of the sound pressure is transmitted to the cochlea. Combining the loss due to going from the air tube into the middle ear and going from the air in the middle ear to the input to the cochlea can result in less than 1% of the sound generated by the output transducer of the hearing aid going into the cochlea.

In contrast to this, the liquid filled tube of the present invention suffers substantially no loss if the bore of the tube is the same as that of the cochlea at the operative intersection of the end of the tube with the cochlea. Further, the loss is only 36% if the bore of the tube is one-half the bore of the cochlea at the operative intersection. Thus as much as 64% of the sound energy created by the output transducer of the present invention is transmitted into the cochlea even when the bore of the tube is only one-half that of the cochlea at the operative intersection.

Another problem with introducing amplified sound into the middle ear space through a tube is the opposing operation of the oval and round windows of the cochlea. Because the cochlea is essentially rigid and is filled with an essentially incompressable liquid, transmittal of sound waves into the liquid through the oval window without a pressure relief would be difficult. The relief is provided by the round window in the cochlea. When the sound waves are transmitted to the oval window by the stapes as occurs in a normal ear, the round window moves in the opposite direction. However, when amplified sound is directed into the middle ear space, the motion of the two windows oppose each other instead of moving cooperatively. This can result in a further loss in sound power transmitted into the cochlea.

Figure 2:
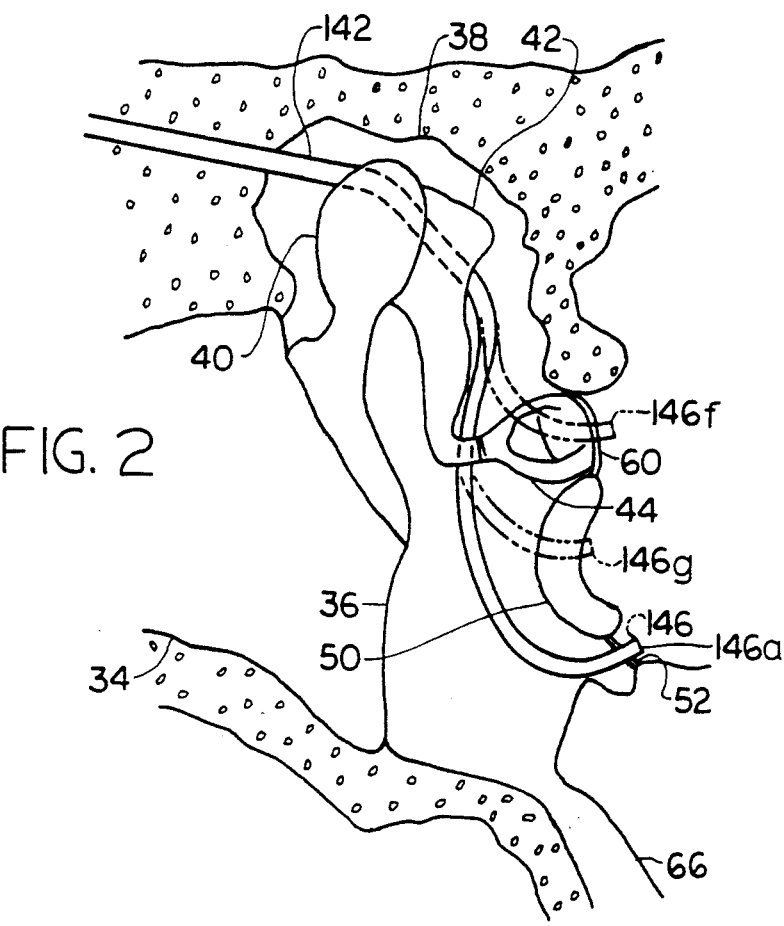
FIG. 2 is an enlarged sectional view of the middle ear cavity showing several positions of the liquid transmission means of the present invention.

FIG. 2 is an enlarged sectional view of the middle ear cavity 38 illustrating the distal end 146 of the liquid filled tube 142 of the present invention led around the malleus 40 and the incus 42 and surgically inserted through the membrane covered round window 52 to the position 146a. Alternatively, the distal end 146 may be surgically inserted through the stapes 44 and oval window 60 to the position 146f. Or the distal end 146 may be surgically inserted by a fenestration through the promontory 50 to the position 146q, or through the vestibule. The tube 142 may be of a biologically inert material such as silicone elastomer sold under the trademark Silastic by Dow Corning Corporation.

Figure 3A:
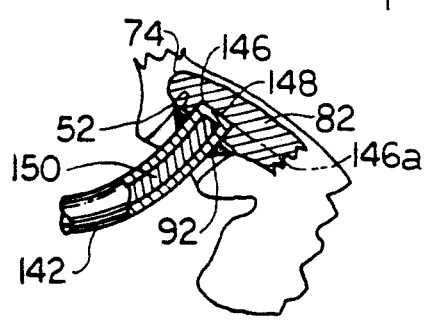
FIGS. 3A, B, C, D, and E are sectional views illustrating various terminations of the liquid transmission means with respect to the round window.

FIGS. 3A, B, C, D, and E show various terminations of the liquid filled tube 142, 142' with the round window 52 and the perilymph 82 of the scala tympani 72. In FIG. 3A the distal end 146 penetrates the round window 52 placing the membrane 148 in contact with the perilymph 82 in position 146a. The membrane 148 closes the distal end 146 of the tube 142 which is filled with a liquid 150. Because the impedance of the liquid 150 is selected to substantially match the impedance of the perilymph 82, virtually no sound pressure is lost at the membrane 148. The tube 142 is held in place with a biologically compatible sealing material 92 well known to the art such as Gelfoam sold by Upjohn, cartilage, perichondrium, mucosal seal, blood clot, fat and (for silicon tubing) Silastic 7-2947 by Dow Corning. Alternatively, the tube 142 may be surrounded by materials such as titanium or synthetic bone which are capable of being bonded by natural bone.

Figure 3B:
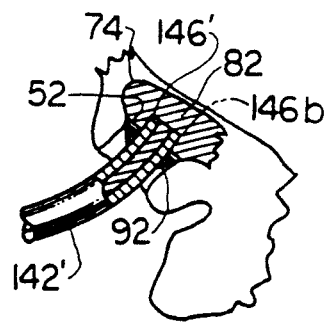
FIGS. 3F, G, H, I, and J are sectional views illustrating various terminations of the liquid transmission means with respect to the oval window.
FIGS. 3K, L, M, N, and P are sectional views illustrating various terminations of the liquid transmission means with respect to the oval window after the stapes is removed.
FIGS. 3Q, R, S, T, and U are sectional views illustrating various terminations of the liquid transmission means with respect to an aperture opened by surgical fenestration in the vestibule or promontory.
Figure 3C:
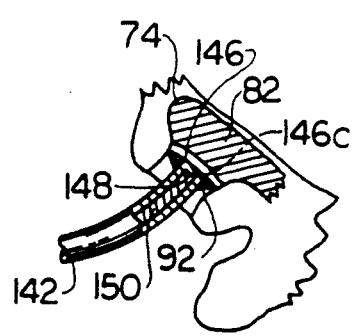
Figure 3D:
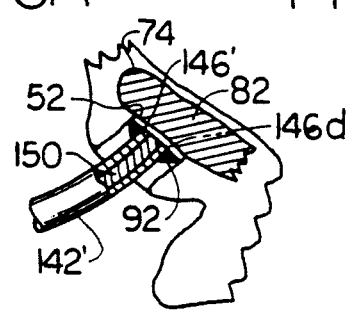
Figure 3E:
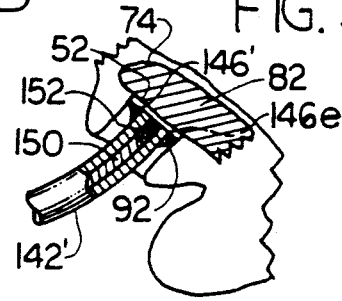

FIG. 3B is similar to FIG. 3A except the tube 142' has an open distal end 146', placed in position 146b, allowing perilymph 82 to fill the tube 142'. FIG. 3C shows the distal end 146 of the liquid filled tube 142 placed against the round window 52 in position 146c. The membrane 148 abuts the round window 52. Because the impedance of the liquid 150 is selected to substantially match the impedance of the perilymph 82 as is the case in FIG. 3A, virtually no sound pressure is lost due to the membranes 148 and 52. FIG. 3D is similar to FIG. 3C except the tube 142' has an open distal end 146' placed in position 146d abutting the round window 52. Finally, FIG. 3E is similar to FIG. 3D except the distal end 146' of the liquid filled tube 142' is filled with a seal 152.

Figure 3F:
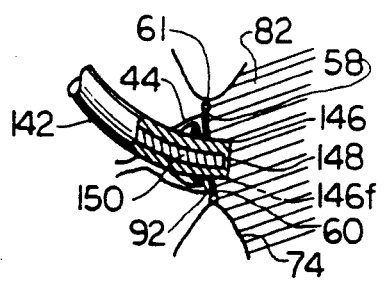
Figure 3G:
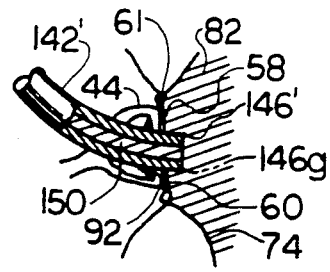
Figure 3H:
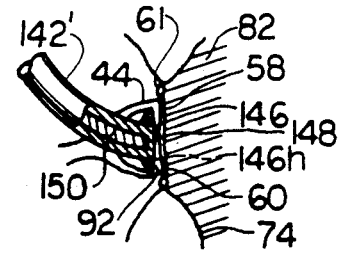
Figure 3I:
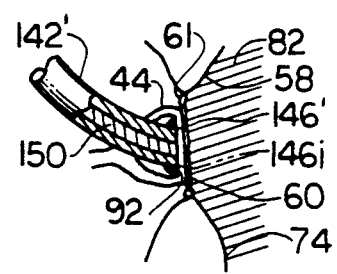
Figure 3J:
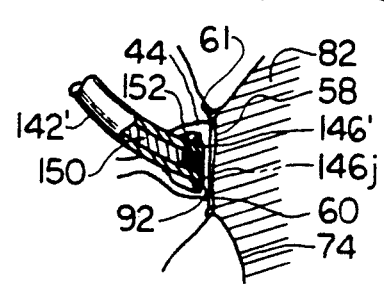

FIGS. 3F, G, H, I, and J illustrate various terminations of the liquid filled tube 142, 142' with the stapes footplate 58, the oval window 60, and the perilymph 82 of the scala vestibuli 74. These figures indicate the distal end embodiments 146, 146' in positions 146f, 146g, 146h, 146i, and 146j which are similar to positions 146a, 146b, 146c, 146d, and 146e of FIGS. 3A, B, C, D, and E with the stapes footplate 58 and the oval window 60 replacing the round window 52.

Figure 3K:
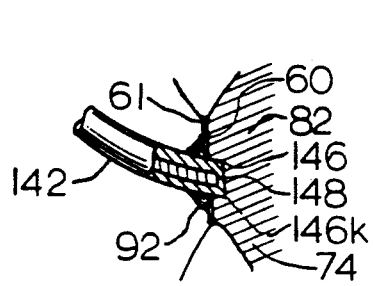
Figure 3L:
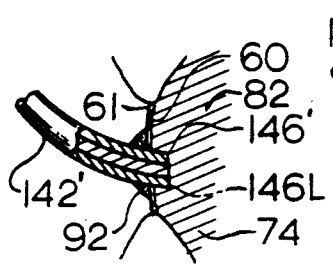
Figure 3M:
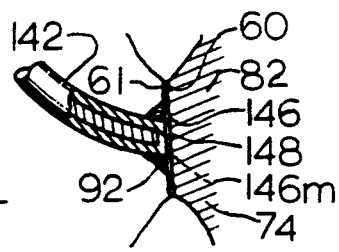
Figure 3N:
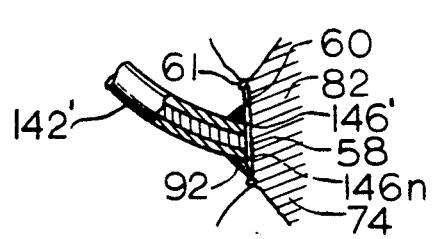
Figure 3P:
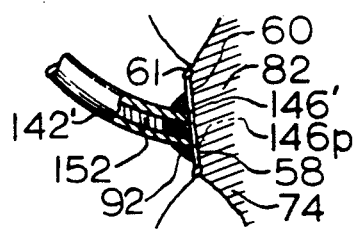

FIGS. 3K, L, M, N, and P illustrate various terminations of the liquid filled tube 142, 142' with the oval window 60 and the perilymph 82 of the scala vestibuli 74 after the stapes has been surgically removed. The figures indicate the distal end 146, 146' in positions 146k, 146l, 146m, 146n, and 146p which are similar to position 146f, 146g, 146h, 146i, and 146j of FIGS. 3F, G, H, I, and J with the stapes 44 removed.

Figure 3Q:
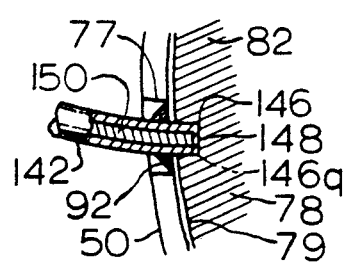
Figure 3R:
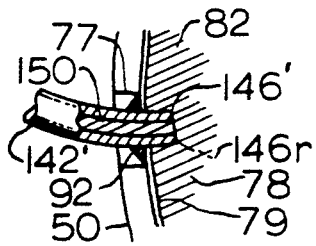
Figure 3S:
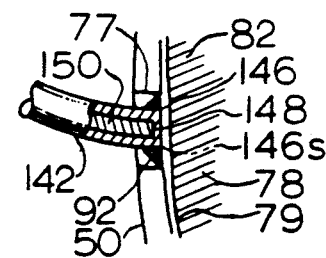
Figure 3T:
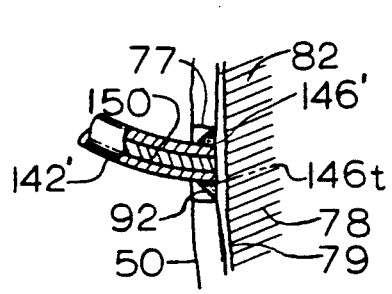

FIGS. 3Q, R, S, T, and U illustrate termination of the liquid filled tube 142, 142' with the perilymph 82 through an aperture 77 in the vestibule or promontory 78. The aperture is opened in the cochlea by surgical fenestration. The figures indicate the distal end embodiments 146, 146' in positions 146q, 146r, 146s, 146t, and 146u which are similar to 146a, 146b, 146c, 146d, and 146e of FIGS. 3A, B, C, D, and E with the lining 79 replacing the round window 52.

Figure 3U:
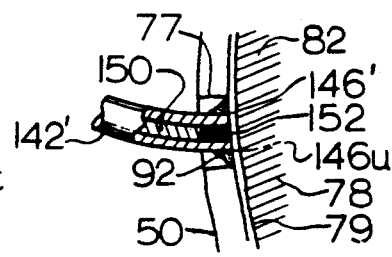

The positions 146a, f, and q for the distal end 146 shown in FIG. 2 correspond to the same positions illustrated in FIGS. 3A, F, and Q. The tube 146' illustrated in FIGS. 3B, G, L, and R is filled with perilymph 82. In the remaining illustrations from FIG. 3A to FIG. 3U, the tubes 142, 142' are filled with a liquid 150 which may be sea water, water containing salt and/or other substances, cerebro-spinal fluid, synthetic perilymph, or the perilymph of the hearing aid 100 wearer. In all cases it is preferrable for the liquid to have acoustic properties substantially similar to the acoustic properties of natural perilymph.

Figure 4:
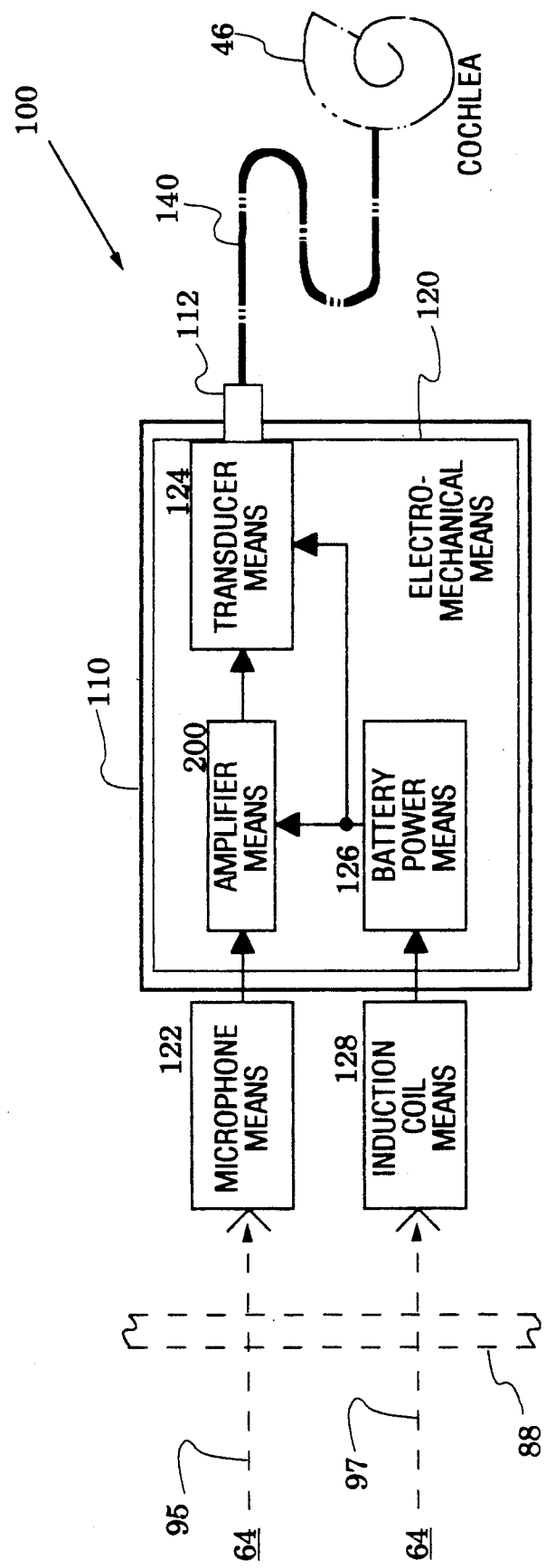
FIG. 4 is a block diagram of an embodiment of the present invention.

FIG. 4 is a block diagram of an embodiment of the present invention. Acoustical energy is imparted to the cochlea 46 via the liquid transmission means 140 by the electro-mechanical means 120. Acoustical energy represented by the arrow 95 from the outer environment 64 passes through the skin flap 88 and is converted by the microphone 122 to electrical signals which are amplified by the amplifier 200 and transformed to mechanical motion by the transducer 124 which may be immersed in the same or similar liquid as in the tube 140. The coupler 112 allows the engagement and disengagement of the transducer 124 to the liquid transmission means 140 without loss of the liquid in the transmission means which would otherwise occur when the electro-mechanical means is removed for servicing. Power is supplied by the battery power means 126 which can be recharged by currents induced by magnetic fields represented by arrow 97 into the induction coil means 128 through the skin flap 88. The electro-mechanical means 120 is mounted in the enclosure 110 which may be of a biologically inert material such as titanium.

The transducer means 124 may be any of those well known in the art including the constant displacement type where the displacement is proportional to the applied voltage. Examples are piezo-electric, magnetostrictive and capacitive transducers. The microphone means 122, induction coil means 128, and the battery power means 126 may be any of those well known in the art.

Figure 5:
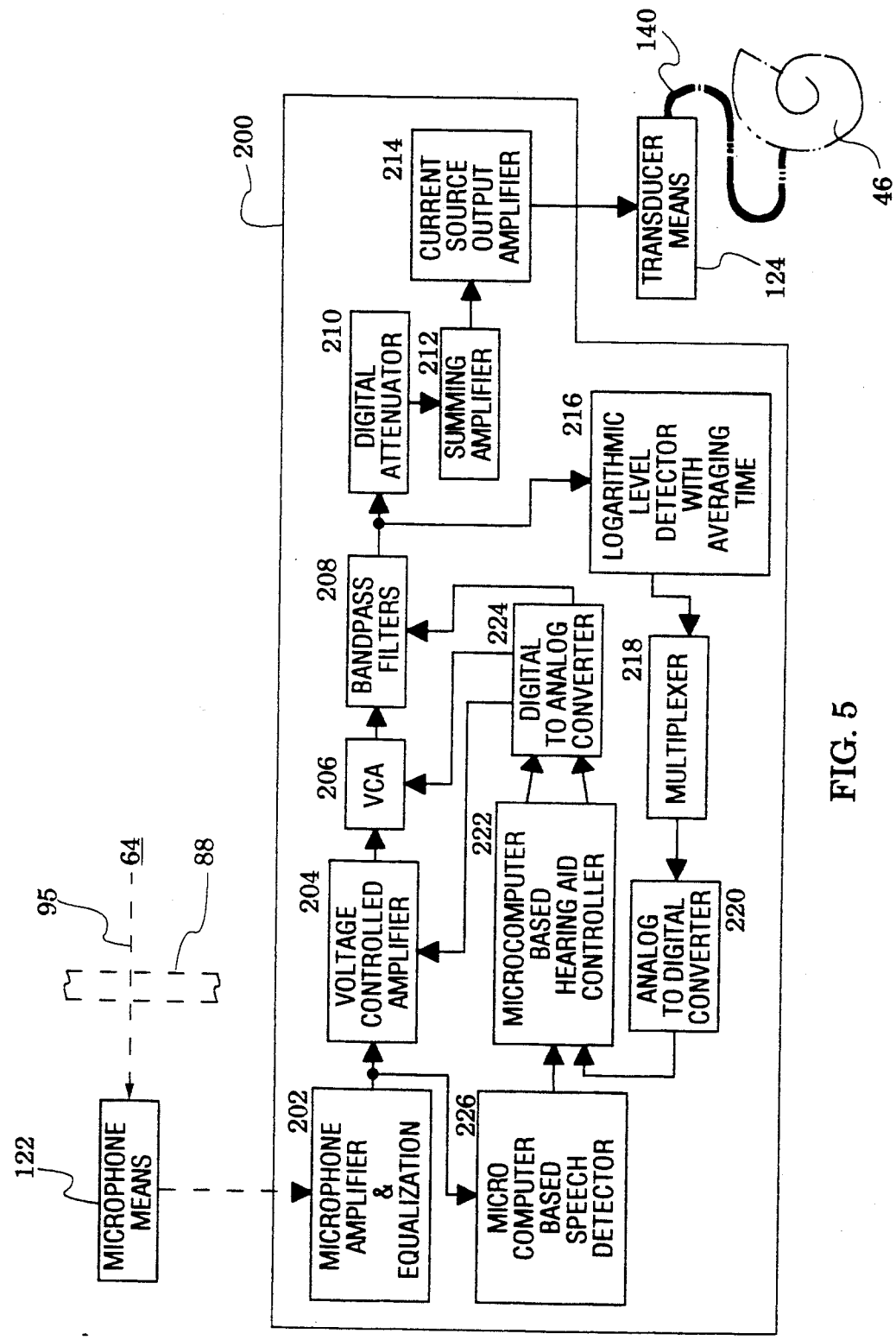
FIG. 5 is a block diagram of an embodiment of the amplifier means of the present invention.

FIG. 5 is a block diagram of the amplifier means 200. Input signals from the microphone 122 are amplified by a microphone amplifier and equalization circuit 202 and then go to a processor 222 controlled VCA (voltage controlled amplifier) 204. The signal is then split up into two or more frequency bands each of which has a voltage controlled amplifier 206 at its input. This provides control of the frequency spectrum from control signals obtained from the processor 222. The output from each band 208 can be preset from the band attenuator 210. The output from each band is then summed in summing amplifier 212 and goes to the current source output amplifier 214 providing the electrical signal to the output transducer 124.

In a completely separate circuit, the signal level of each band is sequentially averaged through logarithmic detector 216, the value of the average is determined, and the result is converted to a digital signal which can then be compared to the previously stored reference value for that band. The microprocessor 222 then adjusts the voltage applied to each band voltage control amplifier so as to achieve at all times the level for that band that has been preset into the microprocessor 222.

The overall input level is measured in another circuit having a speech detector 226. When the preset algorithm determines that speech is not present, the hearing aid is put in standby mode to reduce noise and save battery power.

Many of the features of the amplifier means 200 including the ability to a) control amplification in accordance with a set of predetermined instructions; b) reduce noise by selected frequency band limiting; and c) conserve operating power using speech detection means to activate the hearing aid were disclosed by the present inventor in U.S. Pat. No. 4,596,902.

Thus it may be seen that a hearing aid has been provided having liquid transmission means for substantially matching the impedance of orifices of the cochlea so as to transmit acoustical energy thereto. The liquid transmission means may be a liquid filled tube which may be placed in operative contact with various parts of the hearing system.

Although the present invention has been described with reference to preferred embodiments, numerous modifications and rearrangements can be made with the equivalent result still embraced within the scope of the invention.

What is claimed is:

1. An acoustical transmission means for transmission of acoustical energy to the cochlea, comprising:
    liquid conduction means for conducting acoustical energy therealong; and
    impedance matching means, terminating said liquid conduction means and adapted to be disposed in direct operative association with a window or aperture in the cochlea, for introducing said acoustical energy therethrough.

2. An acoustical transmission means as defined in claim 1 wherein said liquid conduction means comprises:
    a tube defining a bore therethrough; and
    a liquid filling said bore.

3. An acoustical transmission means as defined in claim 2 wherein said liquid is sea water.

4. An acoustical transmission means as defined in claim 2 wherein said liquid is water containing salt and other substances to make it acoustically similar to perilymph.

5. An acoustical transmission means as defined in claim 2 wherein said liquid is silicone having acoustic properties substantiality similar to the acoustic properties of perilymph.

6. An acoustical transmission means as defined in claim 2 wherein said liquid is perilymph of the cochlea of the hearing aid wearer.

7. An acoustical transmission means as defined in claim 2 wherein said liquid is synthetic perilymph.

8. An acoustical transmission means as defined in claim 2 wherein said tube comprises Silastic.

9. An acoustical transmission means as defined in claim 2 wherein said impedance matching means comprises:
    a tube end defined by said tube wherein said bore therein is substantially circular and has a diameter substantially one-half the diameter of said window or aperture which said tube end is disposed at an operative intersection therewith; and
    means for sealing said intersection.

10. An acoustical transmission means as defined in claim 2 wherein said impedance matching means comprises:
    a tube end defined by said tube wherein said bore therein is substantially circular and has a diameter substantially greater than one-half the diameter of said window or aperture which said tube end is disposed at an operative intersection therewith; and
    means for sealing said intersection.

11. An acoustical transmission means as defined in claim 10 wherein said impedance matching means further comprises a membrane defined by said tube across said tube end.

12. An acoustical transmission means as defined in claim 10 wherein said sealing means comprises a biologically compatible sealing material arranged to seal said intersection.

13. An acoustical transmission means as defined in claim 12 wherein said sealing material comprises Silastic 7-2947.

14. An acoustical transmission means as defined in claim 12 wherein said window or aperture is the round window of the cochlea, said tube end abuts said round window and said sealing material is arranged to conform with said tube end and said round window to seal said intersection therebetween.

15. An acoustical transmission means as defined in claim 12 wherein said window or aperture is the round window of the cochlea, said tube end penetrates said round window and said sealing material is arranged to conform with said tube end and said round window to seal said intersection therebetween.

16. An acoustical transmission means as defined in claim 15 wherein said bore at said tube end is open and said bore is filled with perilymph from the cochlea.

17. An acoustical transmission means as defined in claim 12 wherein said window or aperture is the oval window of the cochlea, said tube end abuts said oval window and said sealing material is arranged to conform with said tube end and said oval window to seal said intersection therebetween.

18. An acoustical transmission means as defined in claim 12 wherein said window or aperture is the oval window of the cochlea, said tube end penetrates said oval window and said sealing material is arranged to conform with said tube end and said oval window to seal said intersection therebetween.

19. An acoustical transmission means as defined in claim 18 wherein said bore at said tube end is open and said bore is filled with perilymph from the cochlea.

20. An acoustical transmission means as defined in claim 18 wherein said window or aperture is an aperture opened in the cochlea by surgical fenestration leaving a lining thereacross, said tube end abuts said lining and said sealing material is arranged to conform with said tube end and said aperture to seal said intersection therebetween.

21. An acoustical transmission means as defined in claim 18 wherein said window or aperture is an aperture opened in the cochlea by surgical fenestration leaving a lining thereacross, said tube end penetrates said lining and said sealing material is arranged to conform with said tube end and said aperture to seal said intersection therebetween.

22. An acoustical transmission means as defined in claim 18 wherein said bore at said tube end is open and said bore is filled with perilymph from the cochlea.

23. A hearing aid, comprising:
electro-mechanical means for converting acoustical energy to mechanical motion characteristic thereof;
liquid conduction means coupled to said electro-mechanical means for conducting said mechanical motion therefrom; and
impedance matching means, terminating said liquid conduction means and adapted to be disposed in direct operative association with a window or aperture in the cochlea for introducing said mechanical motion therethrough.

24. A hearing aid as defined in claim 23 wherein said liquid conducting means comprises:
a tube defining a bore therethrough and a sound input end coupled to said electro-mechanical means for receiving said mechanical motion therefrom; and
a liquid filling said bore.

25. A hearing aid as defined in claim 24 wherein said hearing aid is encased in biologically inert material for implanting adjacent the hearing system.

26. A hearing aid as defined in claim 24 wherein said liquid is sea water.

27. A hearing aid as defined in claim 24 wherein said liquid is water containing salt and other substances to make it acoustically similar to perilymph.

28. A hearing aid as defined in claim 24 wherein said liquid is silicone having acoustic properties substantiality similar to the acoustic properties of perilymph.

29. A hearing aid as defined in claim 24 wherein said liquid is perilymph of the cochlea of the hearing aid wearer.

30. A hearing aid as defined in claim 24 wherein said liquid is synthetic perilymph.

31. A hearing aid as defined in claim 24 wherein said impedance matching means comprises:
a sound output end defined by said tube wherein said bore therein is substantially circular and has a diameter substantially one-half the diameter of said window or aperture which said output end is disposed at an operative intersection therewith; and
means for sealing said intersection.

32. A hearing aid as defined in claim 24 wherein said impedance matching means comprises:
an output end defined by said tube wherein said bore therein is substantially circular and has a diameter greater than one-half the diameter of said window or aperture which said output end is disposed at an operative intersection therewith; and
means for sealing said intersection.

33. A hearing aid as defined in claim 32 wherein said impedance matching means further comprises a membrane defined by said tube across said output end.

34. A hearing aid as defined in claim 32 wherein said sealing means comprises a biologically compatible sealing material arranged to seal said intersection.

35. A hearing aid as defined in claim 34 wherein said window or aperture is the round window of the cochlea, said output end abuts said round window and said sealing material is arranged to conform with said output end and said round window to seal said intersection therebetween.

36. A hearing aid as defined in claim 34 wherein said window or aperture is the round window of the cochlea, said output end penetrates said round window and said sealing material is arranged to conform with said output end and said round window to seal said intersection therebetween.

37. A hearing aid as defined in claim 36 wherein said bore at said output end is open and said bore is filled with perilymph from the cochlea.

38. A hearing aid as defined in claim 34 wherein said window or aperture is the oval window of the cochlea, said output end abuts said oval window and said sealing material is arranged to conform with said output end and said oval window to seal said intersection therebetween.

39. A hearing aid as defined in claim 34 wherein said window or aperture is the oval window of the cochlea, said output end penetrates said oval window and said sealing material is arranged to conform with said output end and said oval window to seal said intersection therebetween.

40. A hearing aid as defined in claim 39 wherein said bore at said output end is open and said bore is filled with perilymph from the cochlea.

41. A hearing aid as defined in claim 34 wherein said window or aperture is an aperture opened in the cochlea by surgical fenestration leaving a lining thereacross, said output end abuts said lining and said sealing material is arranged to conform with said output end and said aperture to seal said intersection therebetween.

42. A hearing aid as defined in claim 34 wherein said window or aperture is an aperture opened in the cochlea by surgical fenestration leaving a lining thereacross, said output end penetrates said lining and said sealing material is arranged to conform with said output end and said aperture to seal said intersection therebetween.

43. A hearing aid as defined in claim 42 wherein said bore at said output end is open and said bore is filled with perilymph from the cochlea.

44. A hearing aid as defined in claim 23 wherein said electro-mechanical means comprises microphone means for receiving said acoustical energy and converting said energy into electrical signals characteristic thereof.

45. A hearing aid as defined in claim 44 wherein said electro-mechanical means further comprises:
amplifier means for amplifying said electrical signals into amplified signals;
transducer means for converting said amplified signals into mechanical motion characteristic thereof; and
battery power means for energizing the hearing aid.

46. A method for improving the hearing of a hearing impaired subject, said method comprising the steps of:
surgically interposing a liquid transmission means from a proximal end thereof to a distal end thereof in operative association with a window or aperture in the cochlea of the subject;
filling the liquid transmission means with liquid;
converting acoustical energy external to the subject into mechanical motion characteristic thereof; and
applying the mechanical motion to the proximal end of the liquid transmission means.

47. A method as defined in claim 46 wherein said surgically interposing step includes sealably penetrating said window or aperture with said distal end.

48. A method as defined in claim 46 wherein said surgically interposing step includes abutting said distal end against said window or aperture.

49. A method as defined in claim 46 wherein said surgically interposing step includes spacing said distal end outside said window or aperture and mechanically connecting said distal end to said window or aperture with a plug.

50. A method as defined in claim 46 wherein said surgically interposing step includes cutting an aperture in the vestible or promontory of the cochlea.

51. A method as defined in claim 46 wherein said method further comprises:
 implanting an electro-mechanical amplification means in the mastoid bone of the subject; and
 said surgically interposing step includes operatively associating said proximal end of said liquid transmission means with said electro-mechanical amplification means.

* * * * *